US005874232A

United States Patent [19]
Weavers et al.

[11] Patent Number: 5,874,232
[45] Date of Patent: Feb. 23, 1999

[54] RELATING TO ASSAY REAGENTS

[75] Inventors: Elizabeth Anne Weavers, Aylesbury, Great Britain; Michael Joseph Powell, Gaithersburg, Mass.

[73] Assignee: Alusuisse Holdings A.G., Neuhausen am Rheinfall, Switzerland

[21] Appl. No.: 979,792

[22] Filed: Nov. 26, 1997

Related U.S. Application Data

[63] Continuation of Ser. No. 261,007, Jun. 14, 1994, Pat. No. 5,736,353, which is a continuation of Ser. No. 115,666, Sep. 2, 1993, abandoned, which is a continuation of Ser. No. 928,638, Aug. 14, 1992, abandoned, which is a continuation of Ser. No. 724,518, Jun. 28, 1991, abandoned, which is a continuation of Ser. No. 494,960, Mar. 15, 1990, abandoned, which is a continuation of Ser. No. 334,799, Apr. 3, 1989, abandoned, which is a continuation of Ser. No. 156,580, Feb. 17, 1988, abandoned, which is a continuation of Ser. No. 937,061, Nov. 6, 1986, abandoned.

[30] Foreign Application Priority Data

Mar. 7, 1985 [GB] United Kingdom .................. 8505899
Mar. 7, 1986 [GB] United Kingdom .... PCT/GB86/00129

[51] Int. Cl.$^6$ .............................. C12Q 1/28; C12Q 1/00; G01N 33/53
[52] U.S. Cl. ............................. 435/28; 435/4; 435/975; 536/51; 536/1.1; 534/822; 514/59
[58] Field of Search ................. 435/28, 4, 975; 536/51, 1.1; 534/822; 514/59

[56] References Cited

U.S. PATENT DOCUMENTS

| | | | |
|---|---|---|---|
| 4,252,896 | 2/1981 | Shaffar | 435/22 |
| 4,312,834 | 1/1982 | Vogel et al. | 435/22 |
| 4,340,395 | 7/1982 | Magers et al. | 435/22 |
| 4,380,585 | 4/1983 | Magers et al. | 435/22 |
| 4,448,882 | 5/1984 | Brodbeck et al. | 435/22 |
| 4,451,563 | 5/1984 | Kaufman | 435/22 |
| 4,503,143 | 3/1985 | Gerber | 435/22 |
| 4,596,770 | 6/1986 | Parham et al. | 435/22 |
| 4,598,070 | 7/1986 | Ohwaki et al. | 435/22 |
| 4,654,299 | 3/1987 | Lentfer | 435/22 |
| 5,736,353 | 4/1998 | Weavers et al. | 435/28 |

FOREIGN PATENT DOCUMENTS

| | | |
|---|---|---|
| 70992 | 2/1983 | European Pat. Off. . |
| 123902 | 11/1984 | European Pat. Off. . |
| 104556 | 6/1984 | Japan . |

OTHER PUBLICATIONS

Chemical Abstracts, vol. No. 3, (Jul. 19, 1982), The horse-radish peroxidase–catalyzed oxidation of 3,5,3', 5'-tetramethlybenzidine. Free radical and and charge–transfer complex intermediates, p. 349, Abstract No. 19747y.

Chemical Abstracts, vol. 99, No. 5, (Aug. 3, 1983), Promotion of charge–transfer complex formation by β–or γ–cyclo-–dextrin, p. 477, Abstract No. 37906v.

Stephen Scypinski et al., *International Laboratory* "Cyclodextrin enhanced luminescene spectroscopy", pp. 60–64 (Apr. 1984).

Saenger, Wolfram, *Angew. Chem. Int. Ed. Engl.,* "Cyclodextrin Inclusion Compounds in Research and Industry", 19, pp. 344–362 (1980).

*Primary Examiner*—Louise N. Leary
*Attorney, Agent, or Firm*—Venable; John W. Schneller

[57] ABSTRACT

We have discovered that the stability of a dilute peroxidase-containing solution is greatly enhanced by the addition of a specific substrate for the peroxidase, in the absence of peroxide. We provide a peroxidase-containing reagent consisting of a buffered aqueous solution comprising a peroxidase or a peroxidase conjugate and a specific substrate for the peroxidase, in the absence of peroxide. The peroxidase may be a free peroxidase but for assay purposes is preferably a peroxidase bound to a specific binding component of an assay, to form a peroxidase conjugate. The peroxidase conjugate is preferably a conjugate between a peroxidase and an antigen or an antibody, most preferably an antibody. The peroxidase is preferably horseradish peroxidase.

6 Claims, No Drawings

RELATING TO ASSAY REAGENTS

This is a continiuation of application Ser. No. 08/261,007, filed Jun. 4, 1994, now U.S. Pat. No. 5,736,333 which is a continuation of application Ser. No. 08/115,666, filed Sep. 2, 1993, which is a continuation of application Ser. No. 07/928,638, filed Aug. 14, 1992, which is a continuation of application Ser. No. 07/724,518, filed Jun. 28, 1991, which is a continuation of application Ser. No. 07/494,960, filed Mar. 15, 1990, which is a continuation of application Ser. No. 07/334,799, filed Apr. 3, 1989, which is a continuation of application Ser. No. 07/156,580, filed Feb. 17, 1988, which is a Rule 60 continuation of 06/937,061, filed Nov. 6, 1986, all now abandoned.

This invention relates to improved assay reagents and in particular to an improved peroxidase-containing reagent, an improved peroxidase-substrate reagent and to an assay reagent kit containing one or both such reagents.

The peroxidases are a group of enzymes which catalyse the oxidation of specific substrates by peroxide. Certain substrates, when oxidised in this way, become strongchromophors, generating intense colour. The peroxidases have been widely used as labels in assay application; usually is conjugates with specific binding assay components. The presence of such a labelled component can be readily-detected by adding a substrate solution comprising the specific substrate and a peroxide. An example of an assay employing such a conjugate is the enzyme labelled immunosorbent assay (ELISA), versions of which employ a peroxidase bound to an antibody.

A significant problem in the preparation of assay kits including peroxidase reagents is the long term stability of the peroxidases, particularly in the dilute solutions commonly used for assay. Stability may be enhanced by the inclusion of serum proteins but it has become common to provide peroxidase-containing reagents either in a lyophilised form or as a concentrated solution. The provision of the reagent in this form adds a further manipulation step to the protocol for performing a given assay. It is also known to stabilise peroxidase-containing reagents using serum protein and either 4-aminoantipyrine (see United States patent specification 4448882) or 8-anilino-1-naphthalene sulphonic acid (see British patent specification 2066823).

One of the more widely used peroxidases is horse-radish peroxidase (hereinafter referred to as HRP), for which a specific substrate is tetramethylbenzidine (hereinafter referred to as TMB). TMB is a non-hazardous colourless substrate which forms an intensely coloured oxidation product in the presence of a peroxide and HRP. It is however only sparingly soluble in aqueous solution, and at room temperature tends to crystallize from solution at concentrations suitable for assay. This reduces the availability of TMB for reaction with peroxide and hence reduces the sensitivity of the assay. The known assay kits, which employ TMB as a substrate for HRP, provide a multi-component substrate-reagent pack which must be mixed shortly before use. Any excess reagent cannot be stored for subsequent use.

The catalytic action of peroxidase, as mentioned above, requires the presence of both a specific substrate and a peroxide. We have discovered that the stability of a dilute peroxidase-containing solution is greatly enhanced by the addition of a specific substrate for the peroxidase, in the absence of peroxide.

According to a first aspect of the invention we provide a peroxidase-containing reagent consisting of a buffered aqueous solution comprising a peroxidase or a peroxidase conjugate and a specific substrate for the peroxidase, in the absence of peroxide.

The peroxidase may be a free peroxidase but for assay purposes is preferably a peroxidase bound to a specific binding component of an assay, to form a peroxidase conjugate. The peroxidase conjugate is preferably a conjugate between a peroxidase and an antigen or an antibody, most preferably an antibody. The peroxidase is preferably horseradish peroxidase.

The peroxidase conjugate may be prepared using, for example, sulfhydryl-maleimide coupling (Ishikawa, E., (1980), Immunoassay suppl, 1, 1–16; Duncan, R. J. S., et al, Anal. Biochem., 132, 68–73), disulphide-thiol exchange (Carlsson, J., et al, (1978), Biochem, J., 173 723–737), periodate oxidation (Nakane, P. K., et al, (1974), J. Histochem. Cytochem, 22, 1084–1091) or glutaraldehyde coupling (Aurameas, S. (1969), Immunochem., 6, 43–72; Aurameas, S., et al, (1971), Immunochem, 8, 1175–1179).

The peroxide may be any peroxide (for example, an organic peroxide) but is preferably hydrogen peroxide.

The stabilising effect is particularly marked in dilute solution. Preferably the concentration of peroxidase or peroxidase conjugate is between $10^{-6}$ and $10^{-9}$M, and most preferably about $10^{-9}$M (these concentrations being based on peroxidase).

The specific substrate is in an amount effective to stabilise the poxidase or peroxidase conjugate. For example, where the peroxidase is horseradish peroxidase (free or as a conjugate) and the specific substrate is TMB, the amount of TMB is preferably in the range 0.01 to 0.1 mg/ml.

The solution is buffered at a pH compatible with the peroxidase. Preferably the solution is buffered at a pH from pH 4 to pH 8, more preferably from pH 5 to pH 7 and most preferably at about pH 6. A suitable buffer is 0.1M sodium acetate with citric acid at pH 6.

The solution preferably includes from 0.1 to 5% (w/v) of serum protein, most preferably about 0.2% (w/v). A suitable serum protein is bovine serum albumin. The serum protein assists stability of the peroxidase and also, where the solution is to be used in an immunoassy application, reduces the level of non-specific binding.

A surfactant may also be included in the solution to assist further in reducing non-specific binding. Suitably from 0.01 to 0.1% (v/v) of a surfactant is added, preferably about 0.02% (v/v). For example, 0.02% (v/v) Tween (Trade Mark) may be included in the solution.

According to a second aspect of the invention we provide a method for stabilising the peroxidase activity of a buffered aqueous solution containing a peroxidase or a peroxidase conjugate, comprising adding to the solution an amount of a specific substrate for the peroxidase, in the absence of peroxide, effective to stabilise the peroxidase activity of the solution.

In the course of research, we have discovered that the solubility of TB in an aqueous medium may be advantageously enhanced by the additon of a particular member of the family of cyclic oligosaccharides known as cyclodextrins.

According to a third aspect of the invention, we provide a TMB peroxidase-substrate reagent consisting of an aqueous solution comprising TMB and β-cyclodextrin in solution.

The β-cyclodextrin acts to solubilise the otherwise sparingly soluble TMB, it is thought, by taking the molecules up into the cavity formed at the centre of the cyclic oligosaccharide.

The TMB is preferably at a concentration suitable for use as a substrate for a peroxidase-containing reagent such as is, for example, the subject of the first aspect of the invention.

Suitably the concentration of TMB is from 0.02 to 0.3 mg/ml, more preferably from 0.02 to 0.1 mg/ml, most preferably about 0.1 mg/ml The β-cyclodextrin is preferably at a concentration effective to solubilise the TMB. Suitably the β-cyclodextrin is at a concentration from 0.025 to 0.25% (w/v), most preferably about 0.25% (w/v).

Preferably the, TMB peroxidase-substrate reagent additionally comprises a peroxide, for example, hydrogen peroxide. The concentration of hydrogen peroxide is preferably from 0.002 to 0.02% (v/v) most preferably about 0.005% (v/v).

The TMB peroxidase-substrate reagent may be buffered to avoid pH fluctuations during mixing of assay reagents.

According to a fourth aspect of the invention we provide a method for preparing a TMB preoxidase-substrate reagent of the third aspect of the invention comprising forming an aqueous solution comprising TMB and β-cyclodextrin. Preferably the TMB is first dissolved in an organic solvent, for example, dimethylsulphoxide (DMSO) and then added to an aqueous soluton including β-cyclodextrin.

One or both of the reagents of the first and third aspects of the invention may be included in an assay reagent kit. Preferably the assay reagent kit is an ELISA kit comprising a horseradish peroxidase-antibody reagent of the first aspect of the invention and a TMB peroxidase-substrate reagent of the third aspect of the invention.

The invention is now illustrated by the following Examples and Comparative Examples.

COMPARATIVE EXAMPLE A

An experiment was conducted to measure the stability of an HRP solution.

A peroxidase solution comprising 0.95 μg/ml HRP in a 0.1M sodium acetate/citric acid buffer (pH 6) with 0.2%. (v/v) bovine serum albumin and 0.02% (v/v) Tween (Trade Mark) was freshly prepared. The enzyme activity was measured by adding 10 μl of the peroxidase solution to 1 ml. of a substrate solution, again freshly prepared, which comprised 0.1 mg/ml TMB and 0.0044% (v/v) hydrogen peroxide in a 0.1M sodium acetate/citric acid buffer (pH 6) and measuring the $OD_{650}$ after 20 seconds. This measurement was repeated after the peroxidase solution had been stored at 37° C. The results are shown in Table 1 below.

EXAMPLE 1

The experiment described in Comparative Example A was conducted with the addition of 0.1 mg/ml TMB to the peroxidase solution. The results are shown in Table 1 below.

TABLE 1

| | $OD_{650}$ | |
|---|---|---|
| | Day 0 | Day 3 |
| Example 1 | 1.020 | 0.588 |
| Comparative Example A | 1.250 | 0.188 |

These results show that the enzyme activity of HRP is 58% conserved when stored in the presence of TMB, compared with 15% activity conservation when stored without TMB.

COMPARATIVE EXAMPLE B

An experiment was conducted to measure the stability of an HRP-antibody conjugate in solution.

HRP was conjugated to a monoclonal antibody (in this Example, a mouse monoclonal antibody having specificity to oestone-3-glucuronide) using an adaptation of the glutaraldehyde method of Avrameas (loc.cit.) 100mg at HRP was dissolved in 500 μl of 0.05 bicarbonate buffer (pH9.5) to which was added 500μl of 11% (W/V) glutaraldehyde prepared in the same buffer. The reaction was conducted at room temperature (20° C.–25° C.) for two hours with gentle shaking. The reaction mixture was then applied to a PD10 column (Pharmacia Ltd) which had previously been equilibrated with 0.5M bicarbonate buffer (pH9.5). Elution was achieved with the same buffer and those fractions containing activated HRP were pooled. Antibody (2–3 mg/ml) in 0.05M bicarbonate buffer (pH9.5) was added to the activated HRP to give a mass ratio of 6:1 of activated HRP to antibody. The reaction was conducted at 4° C. for 16–21 hours after which the antibody-HRP conjugate was purified by gel filtation, typically on a TSIC G3000SN column (Toya Soda, Japan).

A peroxidase conjugate solution comprising an HRP-antibody conjugate at 2nM HRP in a 0.1M sodium acetate/citric acid buffer (pE 6) with 0.2% (v/v) bovine serum albumin and 0.02% (v/v) Tween (Trade Mark) was freshly prepared. The enzyme activity-was measured by adding 20 μl of the peroxidase-conjugate solution of the composition described in Comparative Example A and measuring the $OD_{650}$ after 2 minutes. This measurement was repeated after storing at 37° C. The results are shown in Table 2 below.

EXAMPLE 2

The experiment described in Comparative Example B was conducted with the addition of 0.1 mg/ml TMB to the peroxidase-conjugate solution. The results are shown in Table 2 below.

TABLE 2

| | $OD_{650}$ | | |
|---|---|---|---|
| | Day 0 | Day 1 | Day 16 |
| Example 2 | 0.463 | 0.427 | 0.413 |
| Comparative Example B | 0.486 | 0.008 | 0.000 |

These results show that the enzyme activity of the HRP-antibody conjugate was 89% conserved after 16 days of storage, at an assay concentration, in a buffer containing TMB. This compares with 100% loss of activity in an unstabilised solution, stored for the same time.

COMPARATIVE EXAMPLE C

An experiment was conducted to measure the stability of a TMB substrate solution.

A TMB substrate solution was prepared by taking a 10 mg/ml solution of TMB in dimethyl sulphoxide (DMSO) and diluting it 1:100 into a 0.1M sodium acetate/citric acid buffer (pH 6) to which 0.0044% (v/v) $H_2O_2$ had been added. Samples of the substrate were stored at 4° C., 20° C. and 50° C. and the $OD_{650}$ of aliquots of each sample after mixing with an HRP-antibody conjugate solution (2 nM based on peroxidase) was measured. The results are given in Table 3 below. and are expressed as a percentage of a control (freshly prepared substrate solution).

TABLE 3

| Days Storage | Storage Temperature | | |
|---|---|---|---|
| | 4° C. | RT | 50° C. |
| 0 | 94.7 | 94.7 | 94.7 |
| 3 | 99.1 | 93.3 | 66.2 |
| 7 | 77.2 | 55.6 | 74.6 |
| 21 | 31.4 | 32.7 | 66.3 |
| 33 | 24.3 | 33.7 | 55.8 |

EXAMPLE 3

The experiment described in Comparative Example C was conducted with the addition of 0.25% (w/v) β-cyclodextrin. The results are shown in Table 4 below.

TABLE 4

| Days Storage | Storage Temperature | | |
|---|---|---|---|
| | 4° C. | RT | 50° C. |
| 0 | 46.2 | 46.2 | 46.2 |
| 3 | 55 | 57.1 | 53.9 |
| 7 | 60.9 | 63.4 | 62.5 |
| 21 | 57.1 | 55.4 | 60.5 |
| 33 | 42.8 | 52.7 | 46.9 |
| 62 | 38.5 | — | 32 |

These results show the enhanced storage properties afforded by the use of β-cyclodextrin when compared to the results given for Comparative Example C. No crystallisation of TMB was observed in the experiment described in Example 3.

It will be understood that the invention is described above by way of example only and modifications of detail may be made within the scope of the invention.

We claim:

1. A tetramethylbenzidine peroxidase-substrate reagent comprising an aqueous solution of tetramethylbenzidine and an amount of β-cyclodextrin in an amount sufficient to solubilize the tetramethylbenzidine.

2. The tetramethylbenzidine peroxidase-substrate reagent according to claim 1, further comprising a peroxide.

3. A method for preparing a tetramethylbenzidine peroxidase-substrate reagent comprising forming an aqueous solution comprising tetramethylbenzidine and an amount of β-cyclodextrin sufficient to solubilize the tetramethylbenzidine.

4. The method according to claim 3, wherein tetramethylbenzidine is dissolved in an organic solvent and subsequently added to an aqueous solution containing β-cyclodextrin.

5. A method of increasing the stability of tetramethylbenzidine in an aqueous solution over time comprising adding tetramethylbenzidine to an aqueous solution comprising β-cyclodextrin.

6. The method of claim 5, wherein tetramethylbenzidine is dissolved in an organic solvent and subsequently added to said aqueous solution containing β-cyclodextrin.

* * * * *

UNITED STATES PATENT AND TRADEMARK OFFICE
CERTIFICATE OF CORRECTION

PATENT NO. : 5,874,232
DATED : February 23, 1999
INVENTOR(S) : Elizabeth Weavers et al.

It is certified that error appears in the above-identified patent and that said Letters Patent is hereby corrected as shown below:

<u>Title page,</u>
Item [75] to read -- Inventors: Elizabeth Anne Weavers, Buckinghamshire, Great Britain; Michael Joseph Powell, Gaithersburg, Maryland --.

Signed and Sealed this

Second Day of April, 2002

*Attest:*

JAMES E. ROGAN
*Attesting Officer* — *Director of the United States Patent and Trademark Office*